United States Patent [19]

Charles et al.

[11] Patent Number: 5,976,544
[45] Date of Patent: Nov. 2, 1999

[54] **POLYPEPTIDES AND VACCINES FOR *BORDETELLA* PERTUSSIS AND METHOD OF USE**

[75] Inventors: Ian George Charles; Neti Fraser Fairweather, both of Kent, United Kingdom

[73] Assignee: Medeva Pharma Limited, Surrey, United Kingdom

[21] Appl. No.: 08/474,386

[22] Filed: Jun. 7, 1995

Related U.S. Application Data

[63] Continuation of application No. 08/247,544, May 23, 1994, abandoned, which is a continuation of application No. 08/048,059, Apr. 19, 1993, abandoned, which is a continuation of application No. 07/798,045, Nov. 27, 1991, abandoned, which is a continuation of application No. 07/576,589, Sep. 4, 1990, abandoned.

[30] Foreign Application Priority Data

Sep. 4, 1989 [GB] United Kingdom .................... 8919940
May 21, 1990 [GB] United Kingdom .................... 9011358

[51] Int. Cl.$^6$ .......................... A61K 39/10; A61K 39/385
[52] U.S. Cl. ...................................... 424/192.1; 424/190.1; 424/197.11; 424/240.1; 424/253.1; 424/254.1; 530/300; 530/324; 530/329
[58] Field of Search .............................. 424/240.1, 185.1, 424/190.1, 192.1, 253.1, 254.1; 530/300, 324–330, 350, 395, 403

[56] References Cited

FOREIGN PATENT DOCUMENTS 0162639  11/1985  European Pat. Off. .
0338170  10/1989  European Pat. Off. .
90/01494  2/1990  WIPO .

OTHER PUBLICATIONS

Charles et al Proc. Natl. Acad. Sc. USA 86, 3554–3558, May 1989 "Molecular cloning and charactrization . . . ".
De Magistris et al J. Exp. Med. 168, 1351–1362, 1988 "Dissecting Human T Cell Responses . . . ".
Geysen et al Proc. Natl. Acad. Sci. USA 81, 3998–4002, 1984 "Use of Peptide synthesis to probe . . . ".
Clarke et al Nature 330, 381–384, 1987 "Improved immunogenicity of a peptide epitope after fusion . . . ".
Novotny et al Develop, Biol. Standard 61, 27–41, 1985 "Bordetella Adenylate Cyclase: A Genus . . . ".
Novotny et al Infection and immunitiy, 50, 199–206, 1985 "Adenylate Cyclase Activity of a 68,000 . . . ".
Brennan et al Infection and Immunity 56, 3189–3195, 1988 "Identification of a 60 Kilodalton Nonfimbrial . . . ".
Montaraz et al Infection and Immunity 47, 744–751, 1985 "Identification of a 68 kilodalton Protective . . . ".
Charles et al, Eur. J. Immunol. 21, 1147–1153, 1991 "Identification and characterization of a Protective . . . ".
Roberts et al Infection and Immunity 58, 732–739, 1990 "Construction and Characterization In vivo . . . ".

*Primary Examiner*—Robert D. Budens
*Attorney, Agent, or Firm*—Nixon & Vanderhye P.C.

[57] ABSTRACT

A polypeptide for use in a vaccine against *Bordetella pertussis, B. parapertussis* or *B. bronchiseptica* contains an epitope selected from (a) the amino acid sequence coded for by nucleotides 1885 to 1902 of the P.69 gene of *B. pertussis* CN2992; (b) the corresponding amino acid sequence of another strain of *B. pertussis* or of a strain of *B.parapertussis* or *B. bronchiseptica*; and (c) a modified version of sequence (a) or (b) which has substantially the same antigenicity. The polypeptide is no more than 50 amino acid residues long or is a chimaeric protein composed of a carrier protein sequence and a sequence of no more than 50 amino acid residues which contains the required epitope.

20 Claims, 10 Drawing Sheets

Fig.1

```
           10         20         30         40         50         60
XhoI  *          *          *          *          *          *
      CTCGAGACGT CTATACTTCG GAGCACTGTT GAGCGAAGGC TCATTAGATA TATTTTCTGT
      GAGCTCTGCA GATATGAAGC CTCGTGACAA CTCGCTTCCG AGTAATCTAT ATAAAGACA 70         80         90        100        110        120
       *          *          *          *          *          *
      CATTTTCCTT AACCCAAAAA TAAGGGAGAG GGTCCAAAAA GCGCTCGGAC AACTGTTGAC
      GTAAAAGGAA TTGGGTTTTT ATTCCCCTCT CCAGGTTTTT CGCGAGCCTG TTGACAACTG 130        140        150        160        170        180
       *          *          *          *          *          *
      AGGACTGGCT ATACAGTGTT CACAAAATAG CCAAGCTGAA AATAATGTGT
      CGTGATCCGA TCCTGACCGA TATGTCACAA GTGTTTTATC GGTTCGACTT TTATTACACA
      GCACTAGGCT 190        200        210        220        230        240
       *          *          *          *          *          *
      AGCCTTTAGC TATGTTCAGT TAGTTTGGCT AGCAAAGATA TAAAAGCAGG TCGGAAATAT
      TCGGAAATCG ATACAAGTCA ATCAAACCGA TCGTTTCTAT ATTTTCGTCC AGCCTTTATA 250        260        270        280        290        300
       *          *    BamHI *          *          *          *
      TTATGGGCAT TATTATGCAG AGGATCCACA TGATAAAAAA →AACAGTTGAA TATTCCCTCA
      AATACCCGTA ATAATACGTC TCCTAGGTGT ACTATTTTTT TTGTCAACTT ATAAGGGAGT

310
       *
      AAAATGACTG
      TTTTACTGAC
```

```
        Hind III   Bam HI              GAL7 leader                       Nco I
5' AGCTTGGATCCACATGATAAAAAAAACAGTTGAATATTCCCTCAACC ATGG...
3'            ACCTAGGTGTACTATTTTTTTTGTCAACTTATAAGGGAGTTGGTACC...

...ACATTGACCCTTATAAAGAATTCGGAGCTACTGTGGA             3'
...TGTAACTGGGAATATTTCTTAAGCCTCGATGACACCTCAATG        5'
                                        Mae III
                    HBcAg gene 5' end
```

Fig.4(b)

```
     Nco I M   A   P   P   A   P   K   P   A   P   Q   P   G   P   P   Q   P   P
5'  C ATGG CTCCACCAGCTCCAAAACCTCCACAACCAGGTCCACCACAACCACCA...
3'       CGAGGTGGTCGAGGTTTTGGAGGTGTTGGTCCAGGTGGTGTTGGTGGT...

Q   P   P   Q   P   Q   P   E   A   P   A   P   Q   P
... CAACCACCACAACCACAACCAGAAGCTCCAGCTCCACAACC                3'
... GTTGGTGGTGTTGGTGTTGGTCTTCGAGGTCGAGGTGTTGGGTAC            5'
                                                   Nco I
```

Western blot of soluble proteins from induced yeast cells transformed with:
Lane 1= pWYG7H8F (expressing FMD peptide-HBcAg fusion)
Lane 2= pWYG7H8F
Lane 3= no plasma
Lane 4= pWYG7HBC(expressing HBcAg)

Fig.5

Dot blot analysis of HBP fusion protein after sucrose density gradient centriugation. Fraction 1 is the bottom fraction. Fraction 20 is the top fraction.

POLYPEPTIDES AND VACCINES FOR *BORDETELLA* PERTUSSIS AND METHOD OF USE

This is a continuation of application Ser. No. 08/247,544 filed May 23, 1994, now abandoned, which is a continuation of application Ser. No. 08/048,059 filed Apr. 19, 1993, now abandoned, which is a continuation of application Ser. No. 07/798,045 filed Nov. 27, 1991, now abandoned, which is a continuation of application Ser. No. 07/576,589 filed Sep. 4, 1990, now abandoned.

The present invention relates to vaccines against *Bordetella pertussis*, *Bordetella parapertussis* or *Bordetella bronchiseptica*.

*Bordetella pertussis* is the causitive agent of whooping cough in man, although outbreaks of the disease have been associated with the related organism *Bordetella parapertussis*. *Bordetella bronchiseptica* is primarily an animal pathogen, although it has been isolated from children with whooping cough-like symptoms. Immunisation programmes with whole-cell vaccine of *B. pertussis* have been relatively effective in controlling the disease, although currently the uptake of the vaccine is low in some developed countries because of the reactogenicity associated with vaccination. Clinical symptoms noted for the 1 in 10,000 children suffering side-effects may include persistant screaming, fever and local reactions.

There is a need for a new pertussis a cellular vaccine that lacks the components present in the whole cell vaccine associated with reactogenicity, but still comprises the protective epitopes. The search for the protective components has centered on a number of outer-membrane associated antigens. These include pertussis toxin (ptx Lymphocytosis promoting factor/LPF), filamentous haemagglutinin (FHA), cytotoxic adenylate cyclase (Adcase), dermonecrotic toxin (DNT), tracheal cytotoxin, the agglutinogens (Agg2, Agg3), the 69 kDa outer membrane protein (omp) (P.69) and lipopolysaccharide (LPS).

Much work has been carried out on the pertussis toxin (LPF), which is believed by many to be the most important part of any acellular pertussis vaccine (Bacterial Vaccines, 1984, Chapter 3, Manclark et al. Ed: Germainer). The results of a recent clinical trial in Sweden with an LPF/FHA vaccine showed that such a vaccine provided only about 69% protection (Lancet 1, 995, 1988). This is lower than the results expected for protection provided by a whole-cell vaccine, and resulted in the LPF/FHA vaccine not being licensed by the Swedish Health Authority.

EP-A-0162639 discloses a vaccine formulation for protection against *B. pertussis* which includes an antigenic preparation derived from *B. pertussis* comprising proteinaceous material associated with adenylate cyclase activity (ACAP) together with a pharmaceutically acceptable carrier therefor. An ACAP with a molecular weight of 69 kDa is disclosed.

In order to characterise which regions of this ACAP, termed the P.69 antigen, were important for protection the gene encoding the protein was cloned and sequenced (Charles et al, PNAS, Vol 86, 3554–3558, 1989). P.69 as extracted from *B. pertussis* appears to be the processed form of a 93 kDa precursor (P.93).

The present invention provides a polypeptide suitable for use in a vaccine which polypeptide presents an epitope comprising:

(a) the amino acid sequence coded for by nucleotides 1885 to 1902 of the P.69 gene of *B. pertussis* CN2992;

(b) the corresponding amino acid sequence of another strain of *B. pertussis* or of a strain of *B. parapertussis* or *B. bronchiseptica*; or (c) a said sequence (a) or (b) which has been modified such that the modified sequence has substantially the same antigenicity as that of the said sequence (a) or (b); the said polypeptide being no more than 50 amino acid residues long or being a chimaeric protein having an amino acid sequence comprising the sequence of a carrier protein and a foreign sequence of no more than 50 amino acid residues which comprises the sequence of a said epitope.

The polypeptides of the invention comprise a defined antigenically effective sequence. This sequence is

PGPQPP based on the sequence of the P.69 gene of *B. pertussis* CN2992 disclosed by Charles et al (1989) and using the one letter code for amino acids (Eur. J. Biochem. 138, 9–37, 1984). The sequence therefore essentially consists of amino acid residues 547 to 552 of the P.69 protein of *B. pertussis* CN2992. The corresponding sequence for other strains of *B. pertussis* and for strains of *B. parapertussis* and *B. bronchiseptica* can be readily determined by lining up the amino acid sequence of the P.69 antigen, the P.70 antigen or the P.68 antigen respectively with the P.69 sequence shown by Charles et al (1989).

Preferably the epitope comprises:

(a₁) the amino acid sequence coded for by nucleotides 1876 to 1944 of the P.69 gene of *B. pertussis* CN2992;

(b₁) the corresponding amino acid sequence of another strain of *B. pertussis* or of a strain of *B. parapertussis* or *B. bronchiseptica*; or (c₁) a said sequence (a₁) or (b₁) which has been modified such that the modified sequence has substantially the same antigenicity as that of the said sequence (a₁) or (b₁).

Sequence (a₁) is therefore:

APQPGPQPPQPPQPQPQPEAPAPQP

The sequence represents amino acid residues 544 to 566 of the P.69 protein of *B. pertussis* CN2992. This sequence and the corresponding sequence (b₁) for the P.70 antigen of *B. parapertussis* and the P.68 antigen of *B. bronchiseptica* can be aligned as follows. The PGPQPP epitope is underlined:

P.70 APQPGPQPGPOPPQPPQPPQPPQPPQPPQRQPEAPAPQP

P.68 APQPGPQ<u>PGPOPP</u>QPPQPPQP - - - PQRQPEAPA-PQP

P.69 APQ<u>PGPOP</u>-PQPPQP - - - QPEAPAPQP

The sequences can be modified in such a way that a modified sequence exhibits substantially the same antigenicity as the unmodified sequences. The modified sequence should therefore show a similar or greater degree of effectiveness in the Kendrick test than the corresponding unmodified sequence. A modified sequence has substantially the same amino acid sequence as an unmodified sequence but comprises one or more amino acid substitutions, insertions or deletions.

One or more amino acid residues of a sequence (a), (a₁), (b) or (b₁) as above may therefore be replaced by one or more other amino acid residues which do not affect the antigenicity of the epitope. Consequently, one or more amino acid residue may be replaced by another which preserves the physiochemical character of the original epitope, i.e, in terms of charge density, hydrophilicity/hydrophobicity, size and configuration, and hence preserves the immunological structure. Candidate substitutions are A for G and vice versa; V by A, L or G; K by R; S by T and vice versa; E for D and vice versa; and Q by N and vice versa.

A first type of polypeptide according to the invention is composed of up to 50 amino acid residues, for example up to 40 or up to 30 or up to 20 amino acid residues, which presents an epitope as defined above. Further amino acids may therefore be added to one or both ends of the epitope. one, two, three or four additional residues may be provided at the N-terminus or C-terminus or at both terminii of the defined epitope.

Where additional residues are provided at either or both ends of the epitope, preferably these are the natural residues. These can be deduced from the sequence of the P.69 antigen of B. pertussis, of the P.70 antigen of B. parapertussis or of the P.68 antigen of B. bronchiseptica. Preferred flanking sequences for the epitope are therefore the flanking sequences which naturally occur either side of the amino acid sequence for the epitope in the overall sequence of the P.69, P.70 or P.68 protein as the case may be. Also, a cysteine residue may be provided at the N-terminus or C-terminus. In particular, a cysteine residue may be added to the C-terminus alone. This is in order to facilitate carrier coupling and/or to enhance the immunogenicity of the polypeptide.

The polypeptide may have a free C-terminal carboxy group. Alternatively, it may be in the form of a C-terminal amide. Pharmaceutically acceptable salts of the polypeptide may be employed. The polypeptide may be coupled to a carrier in order to creature an immunogen which is antigenically active. Any appropriate physiologically acceptable carrier may be employed. A conjugate between the polypeptide and the carrier may be formed. The carrier may be for example bovine serum albumin, thyroglobulin, ovalbumin, keyhole limpet hemocyanin (KLH) or hepatitis B core antigen.

A second type of polypeptide according to the invention is a chimaeric protein which presents the defined epitope. The chimaeric protein is typically a carrier protein which has been modified so that its amino acid sequence comprises a foreign sequence of up to 50 amino acids which includes the sequence of the desired epitope. Some amino acids of a protein may be replaced by the foreign amino acid sequence. Alternatively, the foreign amino acid sequence is fused to a protein. An intervening linker of up to 10 amino acids, for example of up to 5 amino acids, may be provided between the epitope and the carrier. The foreign amino acid sequence may vary in length as described for the first type of polypeptide according to the invention.

The epitope is exposed on the surface of the chimaeric protein so that it is presented to the immune system. The chimaeric protein may take the form of a particle or form part of a particulate aggregation. Such an aggregation may comprise plurality of chimaeric proteins and/or may be a viral particle. A protein to which a foreign amino acid sequence comprising the epitope may be fused may be a particle-forming protein such as hepatitis B surface antigen (HBsAg, EP-A-0175261) or hepatitis B core antigen (HBcAg, JP-A-63196299). The foreign sequence may be inserted into the sequence of a viral protein exposed on the surface of the virus (GB-A-2125065). The viral protein may be a capsid protein of a virus.

The foreign sequence may therefore be provided at one of the antigenic sites of a picornavirus such as poliovirus (EP-A-0302801). The epitope may be presented at one of the antigenic sites, for example site 1, 2 or 3, on a capsid protein of an attenuated strain of type 1 poliovirus, or at an antigenic site of type 2 or 3 poliovirus. Other picornaviruses, suitably modified, may be used, e.g. Bovine enterovirus.

The amino acid sequence of an antigenic site of a picornavirus may be replaced completely or partly by the foreign amino acid sequence. Preferably the foreign amino acid sequence is provided in place of some or all of antigenic site 1 of an attenuated strain of type 1 poliovirus. The attenuated strain is typically the Sabin 1 vaccine strain. Antigenic site 1 of a type 1 poliovirus is composed of amino acid residues 91 to 102 of the VP1 capside protein.

The polypeptides of the invention are synthetic polypeptides. They may be prepared by chemical synthesis, in particular the first type of polypeptide of up to 50 amino acid residues long. Solid-phase or solution methods of peptide synthesis may be employed. A polypeptide can be built up therefore by a process comprising condensing single amino acids and/or preformed peptides or two or more amino acids in the order in which amino acids occur in a polypeptide of the invention. The polypeptide may be synthesised so as to possess a free C-terminal carboxy group or a C-terminal amide group. If desired, the polypeptide may be converted into a pharmaceutically acceptable salt.

In solid-phase synthesis, the amino acid sequence of the desired polypeptide is built up sequentially from the C-terminal amino acid which is bound to an insoluble resin. When the desired polypeptide has been produced, it is cleaved from the resin. When solution-phase synthesis is employed, the polypeptide may again be built up from the C-terminal amino acid. The carboxy group of this acid remains blocked throughout by a suitable protecting group, which is removed at the end of the synthesis.

Whichever technique, solid phase or solution-phase, is employed each amino acid added to the reaction system typically has a protected a-amino group and an activated carboxy group. An amino group may be protected by the fluoren-9-ylmethoxycarbonyl (Fmoc) or t-butoxycarbonyl (Boc) group. A carboxy group may be activated as a pentafluorophenyl or 1-oxo-2-hydroxy-dihydrobenzotriazine ester. Each condensation step may be effected in the presence of dicyclohexylcarbodiimide or 1-hydroxybenzotriazole.

Side chain functional groups are typically protected too, for example the side chain amino group of a lysine, the side chain hydroxy group of a threonine or the side chain sulphydryl group of a cysteine. After each step in the synthesis, the a-amino protecting group is removed. However, any side-chain protecting groups are generally only removed at the end of the synthesis although they may be retained if desired.

The polypeptides may be prepared with a C-terminal carboxy or amide group as desired. In solid phase peptide synthesis, this may be determined by how the C-terminal amino acid is linked to the resin support and/or how the final peptide is cleaved from the resin. Typically the resin is a styrene and/or divinylbenzene polymer. The C-terminal amino acid may be linked to the resin via an ester linkage which can be cleaved by a strong acid such as HBr in trifluoroacetic acid or HF to give the peptide with a C-terminal carboxy group. Ammonolysis can give the corresponding amide instead.

An alternative method of obtaining a polypeptide amide by solid phase synthesis is to arrange for the C-terminal amino acid of the polypeptide to be linked to the resin via a peptide aminobenzhydryl bond. This can be formed by coupling with dicyclohexylcarbodiimide and can be cleaved with HF, typically in the cold. For solution phase synthesis, whether a C-terminal carboxy or amide group is present may depend upon how the carboxy group of the C-terminal amino acid is blocked and, at the end of the synthesis, unblocked. A polypeptide with a C-terminal carboxy group can be converted into one with a C-terminal amide group and vice versa.

Both types of polypeptide according to the invention may be prepared by recombinant DNA methodologies, in particular by:

(i) preparing an expression vector which incorporates a DNA sequence encoding the said polypeptide and which is capable of expressing the said polypeptide when provided in a suitable host; and (ii) providing the said vector in the said host such as to enable expression of the said polypeptide to occur.

Thus a DNA sequence encoding the desired polypeptide is provided. An expression vector is prepared which incorporates the DNA sequence and which is capable of expressing the polypeptide when provided in a suitable host. The DNA sequence is located between translation start and stop signals in the vector. Appropriate transcriptional and translational control elements are also provided, in particular a promoter for the DNA sequence and a transcriptional termination site. The DNA sequence is provided in the correct frame such as to enable expression of the polypeptide to occur in a host compatible with the vector.

In the case of a chimaeric protein, a DNA fragment encoding the foreign amino acid sequence is inserted into a vector at a location which enables the epitope of interest to be expressed, as part of the chimaeric protein, exposed on the surface of the protein. The chimaeric protein is then expressed. Cells harbouring the vector are cultured so as to enable expression to occur. Depending on the type of chimaeric protein, the protein may self-assemble into particles.

Any appropriate host-vector system may be employed. The vector may be plasmid. In that event, a bacterial or yeast host may be used for example *E. coli* or *S. cerevisiae*. Alternatively, the vector may be a viral vector. This may be used to transfect cells of a mammalian cell line, such as CHO cells, in order to cause polypeptide expression.

An epitope according to the invention may be linked to one or more helper T-cell (Th-cell) epitopes. A Th-cell epitope is a site capable of eliciting help for antibody production. A Th-cell epitope is capable of binding class II major histocompatibility (MHC) molecules on the surface of host antigen-presenting cells and B-cells subsequently interacting with the T-cell receptor in the form of a trimolecular complex in order to induce B-cells to differentiate and proliferate.

A Th-cell epitope may be linked to the first type of polypeptide of the invention in a variety of ways. Glutaraldehyde polymerisation may be used, in which the polypeptide of the invention is copolymerised with a polypeptide which presents a Th-cell epitope via their amino groups. The polypeptide of the invention and the polypeptide presenting the Th-cell epitope may be conjugated together via a heterobifunctional cross-linking agent such as m-maleimidobenzoyl-N-hydroxy-succinimide ester (MBS).

The polypeptide of the invention may alternatively by linked at its C-terminus or N-terminus to a polypeptide presenting a Th-cell epitope via a peptide bond. This may be achieved by co-linear synthesis of the polypeptide of the invention and the polypeptide presenting the Th-cell epitope or by use of recombinant DNA technology as above to express a fusion protein in which the two polypeptides are fused together. In any of the methods, any suitable Th-cell epitope may be used.

A preferred polypeptide presenting Th-cell epitopes is hepatitis B core antigen (HBcAg). A first type of polypeptide of the invention may be chemically coupled to HBcAg. Recombinant DNA technology can be used to produce a fusion protein according to the second type of polypeptide of the invention, comprising HBcAg to the amino terminus of which is linked the sequence of a polypeptide of the invention. The epitope of interest may be fused directly to the amino terminus of HBcAg. Alternatively, the sequence may be fused to the HBcAg via an intervening linker. Such a linker may be composed of one or more, for example up to ten, amino acid residues.

The polypeptides of the invention are useful as vaccines against *B. pertussis, B. parapertussis* or *B. bronchiseptica*. An effective amount of the polypeptide is administered to a host in need of vaccination. The polypeptide may be administered orally or parenterally, for example subcutaneously or intramuscularly. The polypeptide may be given in association with FHA. In this way, immunity to whooping cough may be induced in a human. Immunity to *B. bronchiseptica* may be induced in a mammal.

Typically, a polypeptide is administered orally or parenterally in an amount of 1 to 1000 μg per dose, more preferably from 10 to 100 μg per dose. A single dose may be given or a plurality of doses may be administered over a period of time. When FHA is administered, it may be used in an amount of 20 to 75 μg per dose. The FHA is typically administered in the same vaccine formulation as the polypeptide of the invention.

A vaccine of the invention comprises a polypeptide of the invention, optionally FHA, and a pharmaceutically acceptable carrier or diluent. The carrier or diluent may be any liquid medium suitable for use as a vehicle to introduce an antigen into a patient, for example an isotonic saline solution. The polypetide may also be present with an adjuvant for stimulating the immune response and thereby enhancing the effect of the vaccine. A suitable physiologically acceptable adjuvant is aluminium hydroxide or aluminium phosphate.

Conveniently the vaccine formulations are presented to contain final concentration of antigenic polypeptide in a range of from 0.01 to 5 mg/ml, preferably 0.03 to 2 mg/ml, most preferably about 0.3 mg/ml. After formulation the vaccine may be incorporated into a sterile container which is then sealed and stored at a low temperature, for example 4° C., or may be freeze-dried.

One or more doses of such a formulation may be administered to a host to be immunised. It is recommended that each dose is from 0.1 to 2 ml, preferably from 0.2 to 1 ml and most preferably about 0.5 ml of vaccine. Immunity can therefore be induced by the administration of an effective amount of a vaccine formulation.

The following Examples illustrate the present invention. In the accompanying drawings:

FIG. 4(*a*) shows the nucleotide sequence of synthetic oligo A containing the GAL7 untranslated leader sequence and the 5' region of the HBcAg gene.

FIG. 4(*b*) shows the nucleotide sequence of synthetic oligo B, encoding the presumed BB05 epitope.

FIG. 5 shows the results of Western blot of soluble proteins in Example 2(6) from induced yeast cells transformed with (1) pWYG7HBF (expressing FMD peptide-HBcAg fusion), (2) pWYG7HBF, (3) no plasmid and (4)

pWYG7HBC (expressing HBcAg). The blot was developed using a rabbit anti-HBcAg serum and a goat anti-rabbit IgG-peroxidase conjugate. The position in the gel of 30K, 21.5K and 14.3 KDa size markers is indicated.

EXAMPLE 1

Preparation of Peptides

The peptides shown below were synthesised using an adaptation of the Merrifield method (Merrifield, JACS, 85, 2149–2154, 1963) described by Houghten (Houghten, PNAS, 82, 5131–5135, 1985):

Peptide 683: APQPGPQPPQPPQPQPEAPAPQP-PAGRELSC (peptide of invention)

Peptide 684: AGRELSAAANAAVNTGGVGLASTLW-YAEC

Peptide 685: TLWYAESNALSKRLGELRLNPDAG-GAWGRGC

Peptide 683 is composed of the amino acids coded for by nucleotides 1876 to 1962 of the P.69 gene and has an additional non-natural carboxy-terminal cysteine residue. Peptide 684 is composed of the amino acids coded for by nucleotides 1948 to 2031 of the P.69 gene and has an additional non-natural carboxy-terminal cysteine residue. Peptide 685 is composed of the amino acids coded for by nucleotides 2014 to 2100 of the P.69 gene and has an additional non-natural carboxy-terminal cysteine residue.

Each peptide was synthesised on a p-methyl-benzhydrylamine divinylbenzene resin. The α-amino protecting group on each amino acid was t-butoxycarbonyl (Boc). Each coupling cycle was as follows:

1. Wash resin with dichloromethane –10 minutes
2. Wash with 5% diisopropylethylamine in dichloromethane –2 minutes ×3
3. Dichloromethane wash –1 minute ×2
4. Couple t-butoxycarbonyl amino acid in dichloromethane, 0.3M diisopropylcarbodiimide –60 minutes. For N and Q coupling was effected in dimethylformamide, 0.3M diisopropylcarbodiimide and 0.125M hydroxybenzotriazole.
5. As 3
6. Deprotect with 50% trifluoroacetic acid in dichloromethane –20 minutes
7. Dichloromethane wash –1 minute ×6
8. Return to 2.

When coupling cycles were completed the peptide was cleaved off the resin using hydrogen fluoride for 1 hour with an anisole scavenger 10%. The peptide was thus obtained with a carboxy-terminal amide group. It was then ether washed, dried, dissolved in 15% acetic acid and lyophilized.

EXAMPLE 2

Expression of B. pertussis Epitope—HBcAg Fusion Protein (HBP) in Yeast

1. General

An amino acid sequence corresponding to nucleotides 1855 to 1944 of the P.69 gene was fused genetically to the amino-terminus of HBcAg. The resulting fusion protein was expressed efficiently in yeast and reacted with monoclonal antibody (Mab) BB05 which was raised against the 68 kDa protein of B. bronchiseptica but cross-reacts with P.69 of B. pertussis. The fusion protein was shown to assemble into core particles and conferred protection against B. pertussis challenge in the Kendrick test, when used in conjunction with FHA.

2. Construction of Yeast Expression Vector pWYG7

The fusion protein was expressed in Saccharomyces cerevisiae from the multi-copy vector pWYG7 which carried the regulated GAL7 promoter. The vector pWYG7, constructed at Wellcome, was used for the expression of HBP, i.e. of a fusion protein composed of a major epitope of P.69 fused to the amino-terminus of HBcAg. Vector pWYG7 is derived from the 2$\mu$ vector pJDB219 (Beggs, Nature 275, 104–109, 1978) modified to contain a kanamycin-resistance marker (kan$^r$) and the yeast galactose-regulated GAL7 promoter.

Figure 1:
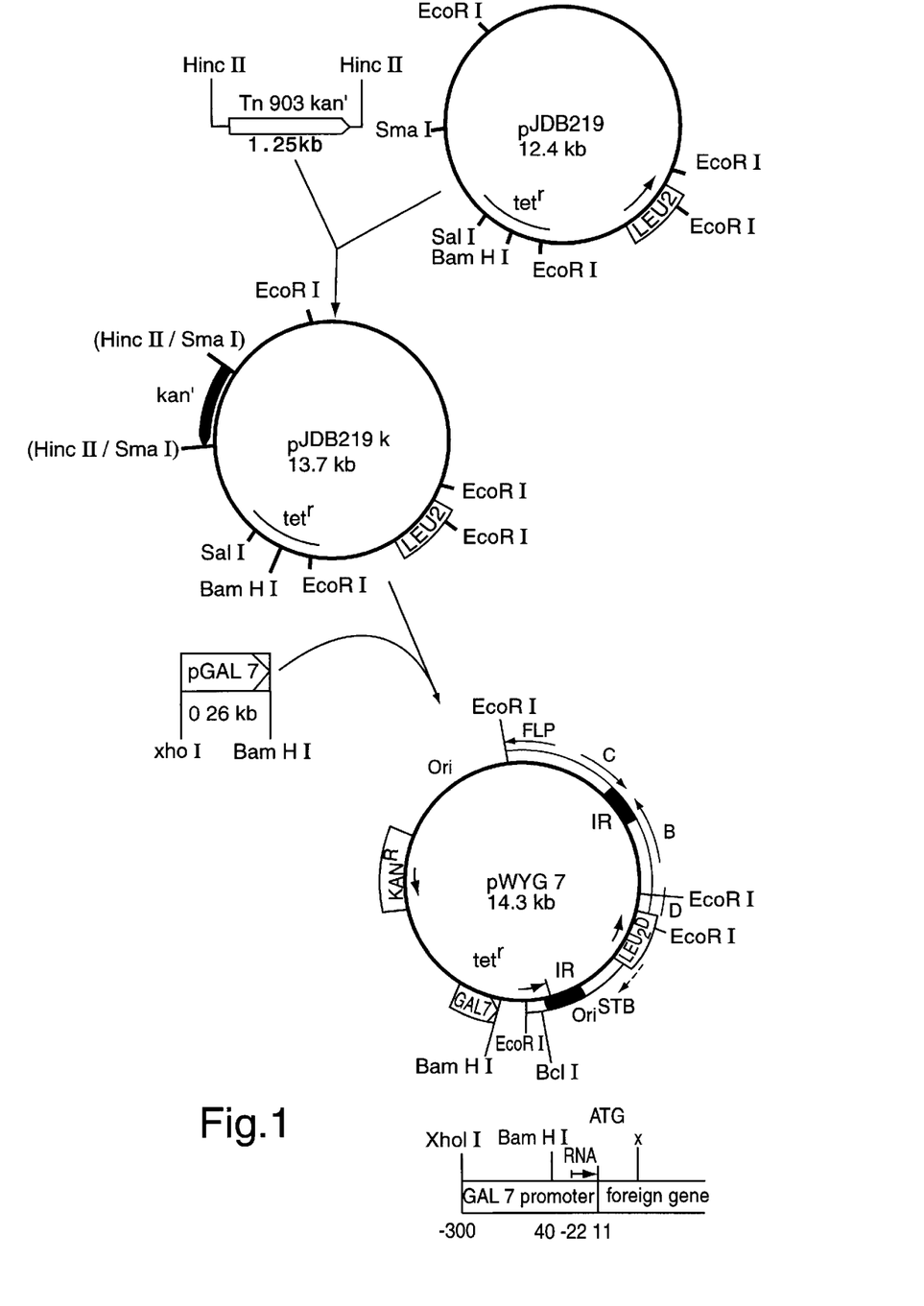
FIG. 1 shows the construction of vector pWYG7.

The construction of pWYG7 is outlined in FIG. 1. First the kan$^r$ marker (HincII fragment from pUC4K; Vieira and Messing, Gene 19, 259, 1982) was ligated into the unique SmaI site of pJDB219 to give the kan$^r$ tet$^r$ vector pJDB219K. Secondly, a synthetic GAL7 promoter fragment (XhoI-BamHI fragment, sequence shown in FIG. 2) was cloned into the unique SalI and BamHI sites of pJDB219K. The resulting vector, pWYG7, has the GAL7 promoter with unique BamHI and BclII sites upstream of the yeast 2$\mu$ plasmid FLP gene transcriptional terminator (Sutton and Broach, Mol. Cell. Biol. 5, 2770–2780, 1985). Foreign genes to be expressed from pWYG7 are inserted between the BamHI and BclI sites. The design of the GAL7 promoter fragment is discussed below.

Figure 2:
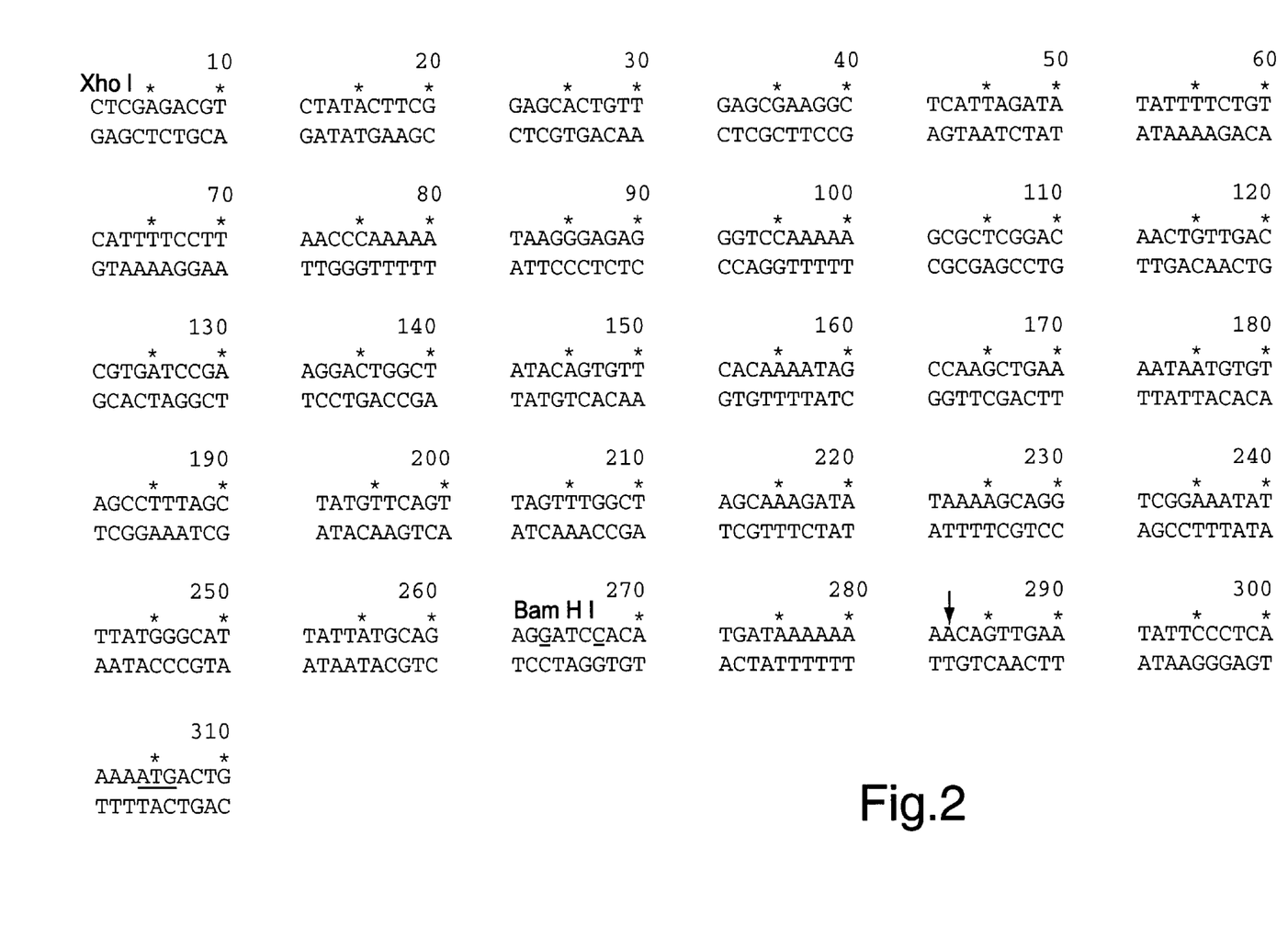
FIG. 2 shows the nucleotide sequence of the promoter region of GAL7. The synthesised promoter corresponds to the XhoI to BamHI fragment. Regions downstream of BamHI are present in native GAL7 including the RNA start site (↓) and the initiating ATG (underlined). The two basepairs which were altered to give a BamHI site are underlined.

The smallest fragment of DNA upstream of the GAL7 gene which exhibits full promoter activity has been defined by deletion mapping (Tajima et al., Yeast 1, 67–77, 1985). Based on this information a 260 bp GAL7 promoter fragment was synthesised (FIG. 2 for sequence). The 260 bp promoter was synthesised as four overlapping oligonucleotides using a Pharmacia Gene Assembler (protocol supplied by Pharmacia). These oligonucleotides were phosphorylated and annealed using standard techniques, then ligated into XhoI-BamHI cut pIC-20H (Marsh et al., Gene 32, 481–485, 1984). Positive clones were identified and their DNA sequenced using the double-stranded DNA sequencing method with universal and reverse sequencing primers (Hong, Biosci. Report 2, 907, 1982). The sequence of the GAL7 inserts was confirmed, and then the XhoI-BamHI GAL7 insert was excised and cloned into pJDB219K as described above.

The design of the GAL7 promoter fragment in pWYG7 is such that the natural GAL7 DNA sequence has been slightly modified (2 bp changed) in order to make the BamHI cloning site upstream of the GAL7 MRNA start sites. The foreign gene to be expressed is then linked with synthetic DNA to the BamHI site, such that the GAL7 mRNA start sites are introduced, along with the GAL7 upstream untranslated sequences. Thus the first non-yeast DNA downstream of the promoter is the initiating ATG codon of the foreign gene, and the transcript produced will have a yeast GAL7 leader rather than a foreign leader which could reduce efficiency of translation.

3. Construction of the HBP Fusion Protein Yeast Expression Vector pWYG7HBP

Figure 3A:
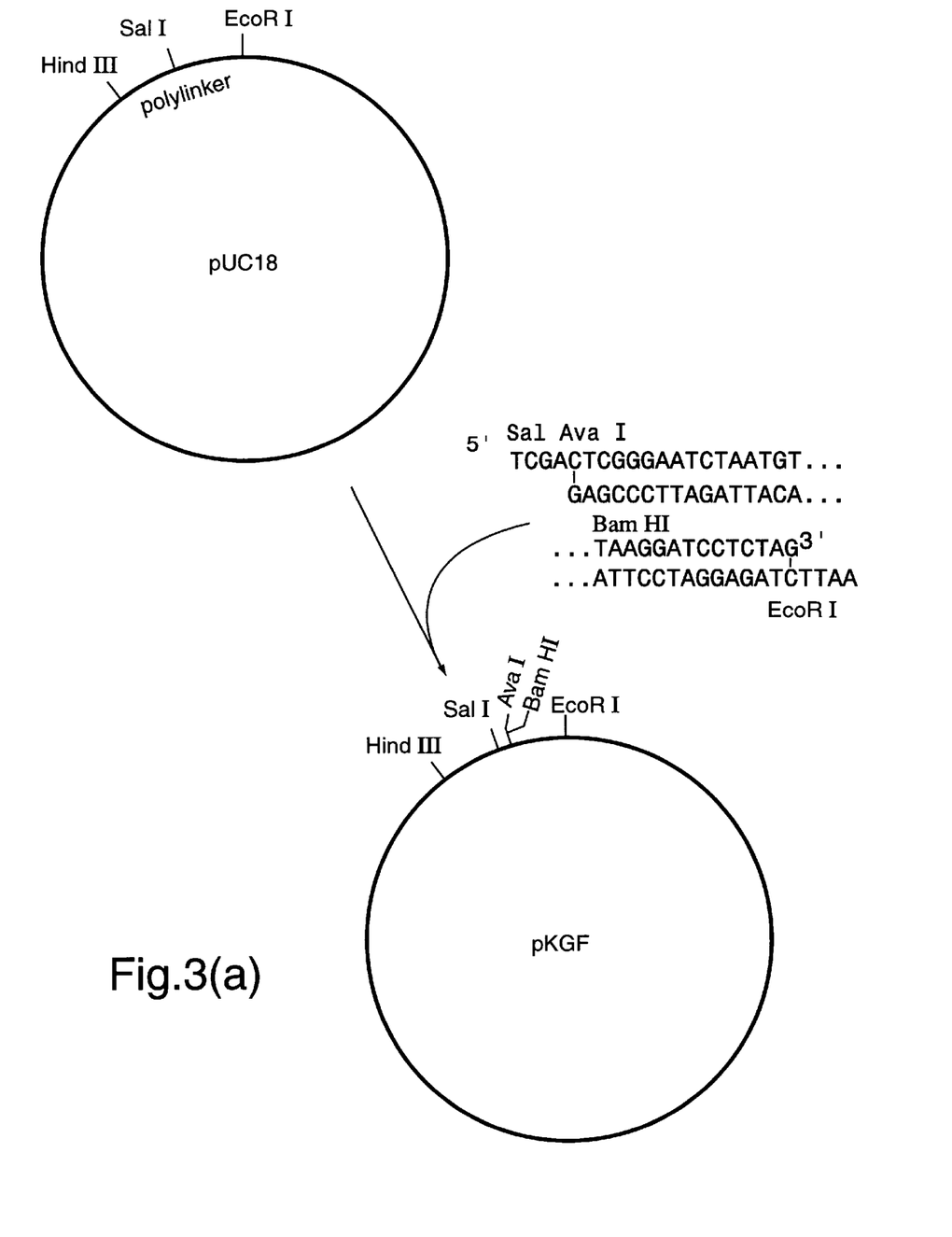
FIG. 3 shows the construction of pWYG7HBP.
Figure 3B:
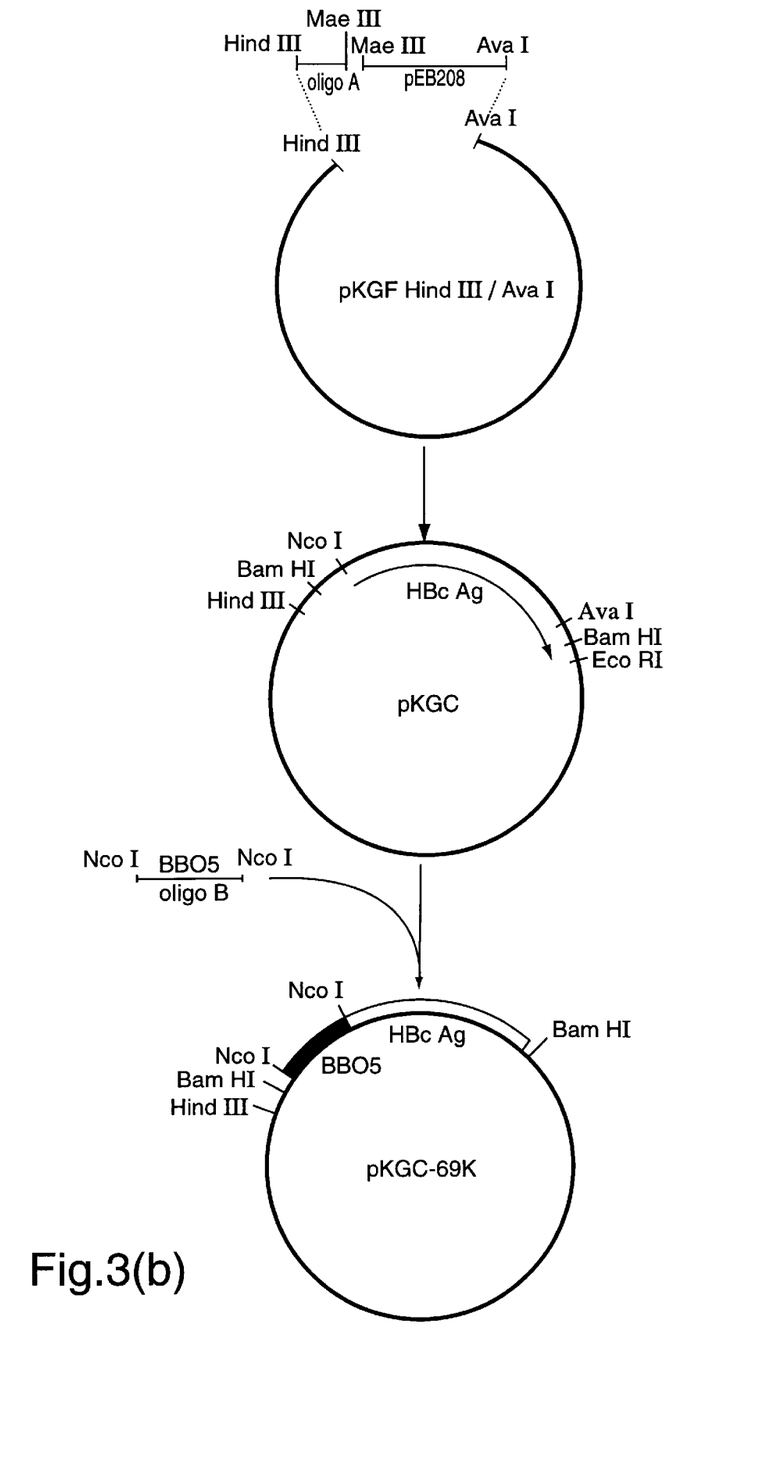
Figure 3C:
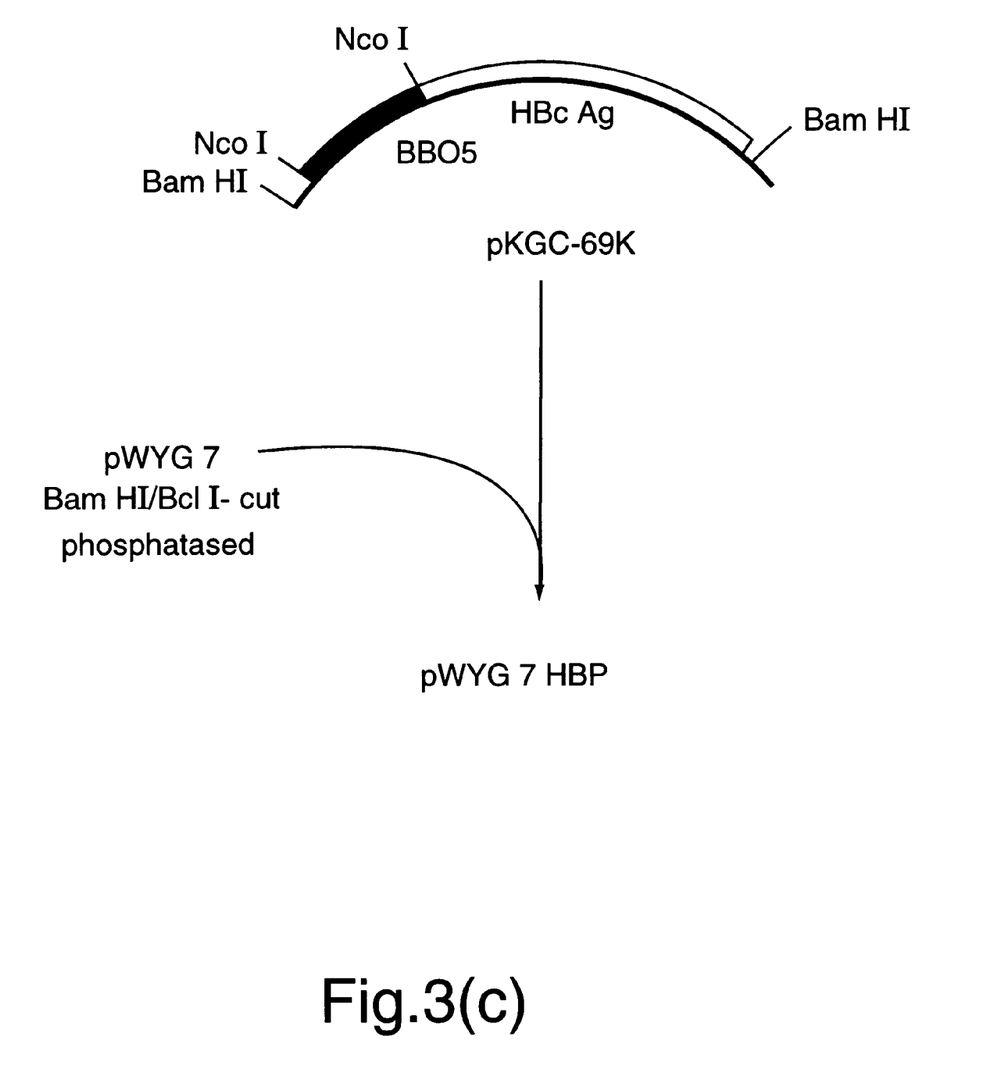

A BamHI-BamHI expression unit for HBP was assembled in an intermediate vector, pKGC-69K. This vector, which contains GAL7 sequences upstream of the initiator ATG codon, was made by first constructing a HBcAg vector, pKGC, with an NcoI (CCATGG) site engineered at the initiator ATG. The DNA encoding the predicted *B. pertussis* epitope was then inserted into this site as a synthetic NcoI-NcoI oligonucleotide linker. The overall scheme for the construction of pKGC, pKGC-69K, and the final expression vector, pWYG7HBP, is shown in FIG. 3.

(i) Construction of pKGC

Figure 4A:
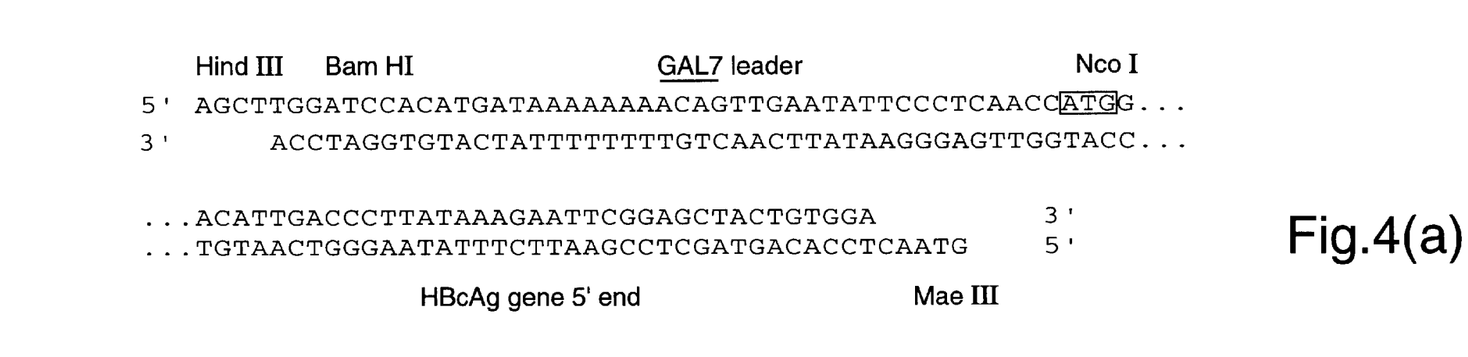

A synthetic SalI-EcoRI linker containing the 3' terminal sequences of HBcAg (AvaI site to stop codon) was ligated between the SalI and EcoRI sites of pUC18 (Vieira and Messing, 1982) to give the plasmid pKGF. The rest of the HBcAg gene was then assembled in pKGF in a three-way ligation: the 2.7 kb HindIII-AvaI fragment of PKGF was isolated and ligated to (i) an 87 bp synthetic (phosphorylated) HindIII-MaeIII fragment (oligoA, FIG. 4a) containing yeast GAL7 upstream sequences and the 5' end of the HBcAg gene, and (ii) a 500 bp MaeIII-AvaI fragment from pEB208 (Clarke et al, Nature 330, 381–384, 1987), which contains most of the central part of the gene. The resulting plasmid, pKGC, is an intermediate vector for expression of HBcAg from pWYG7. The sequence of the synthesised regions of pKGC was confirmed using the double-stranded method with universal and reverse sequencing primers (Hong, 1982).

(ii) Construction of pKGC-69K

Figure 4B:
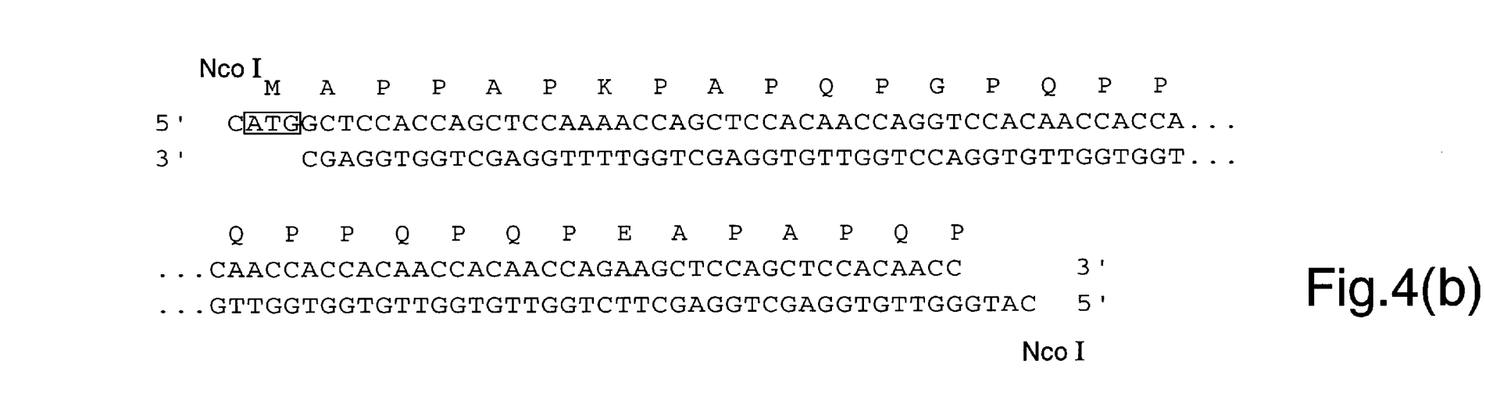
Figure 5:
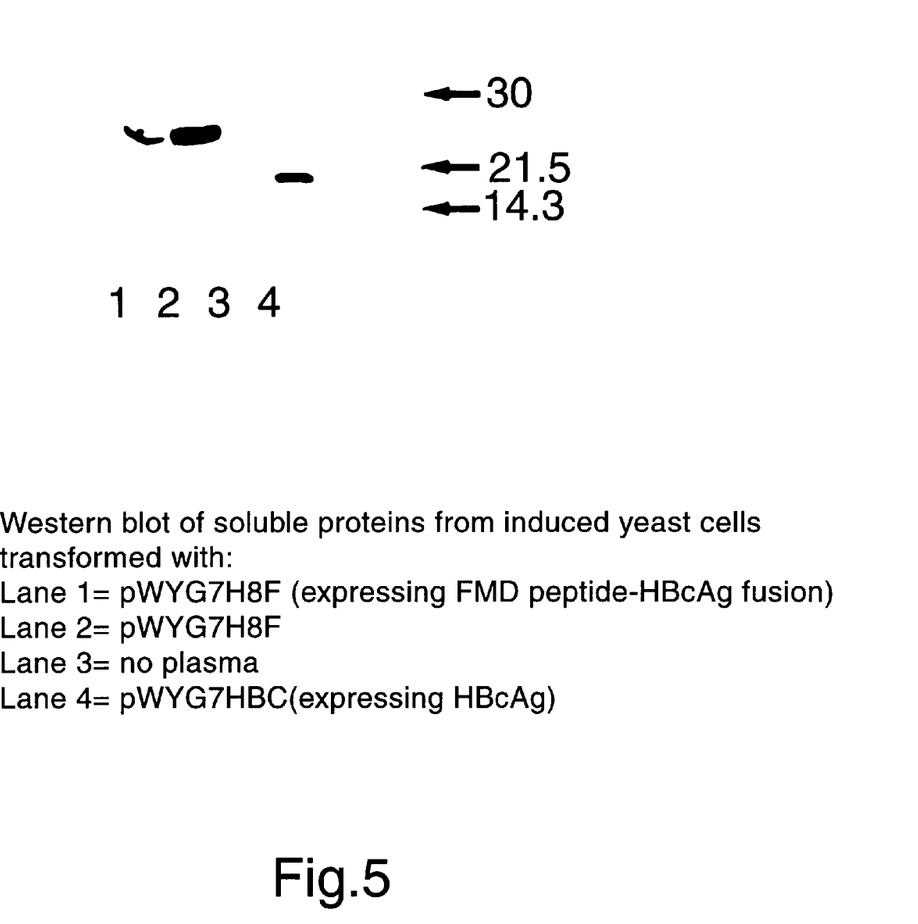
Figure 6:
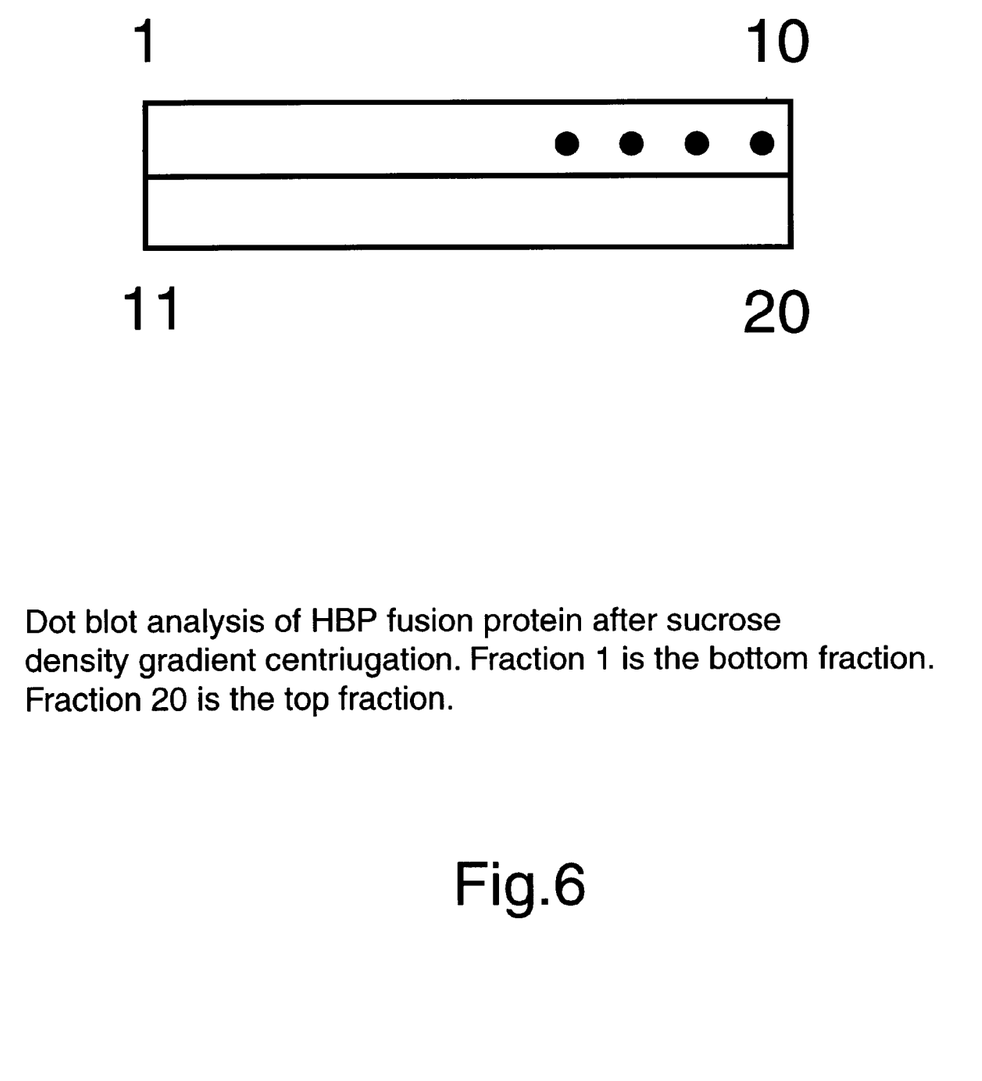
FIG. 6 shows the results of dot blot analysis in Example 2(7) of HBP fusion protein after sucrose density gradient centrifugation. Fraction 1 is the bottom fraction and fraction 20 the top. All the material reacting with the anti-HBcAg serum is in the middle fractions, indicating complete assembly of HBP into particles.

The HBcAg gene in pKGC had been modified to have a unique NcoI (CCATGG) site at the initiator ATG. Therefore N-terminal peptide fusions could be made by inserting suitable NcoI-NcoI DNA fragments at this site. The epitope of the P.69 antigen was predicted to occur at the Pro-rich repeat region, so a suitable pair of oligonucleotides were synthesised to encode this epitope. The oligonucleotides made and the corresponding amino acid sequence are given in FIG. 4b; the *B. pertussis* DNA was altered to give a yeast-optimal codons. pKGC was digested with NcoI, and the annealed, unphosphorylated oligonucleotides were cloned in using the linker-tailing method (Lathe et al, BRL Focus 6, issue 4, 1984). From the resulting plasmids with inserts, ones of the required orientation were selected by double-stranded sequencing of the inserts. The resulting vector, pKGC-69K could be used as a source of a BamHI-BamHI fragment for transfer to pWYG7.

(iii) Construction of pWYG7HBP

The BamHI-BamHI fragment from pKGC-69K was isolated and cloned into pWYG7 ($dam^-$ DNA) that had been digested with BamHI and BclI and then treated with calf-intestinal alkaline phosphatase. After transformation, $Kan^r$ colonies were tested for inserts of the correct orientation, and these plasmids were denoted pWYG7HBP. *E. coli* MC1061 containing pWYG7HBP was deposited on Jul. 28, 1989 at the National Collection of Industrial and Marine Bacteria (NCIMB), Aberdeen, GB under accession number NCIMB 40176.

4. Transformation of Yeast with pWYG7HBP

The vector pWYG7HBF was introduced into the *Saccharomyces cerevisiae* strain S150-2B (a, leu2, his3, ura3, trpl, McCleod et al., Cold Spring Harbor Symp. Quant. Biol. 49, 779–787, 1984) using the lithium transformation procedure of Ito et al. (J. Bact. 153, 163–168, 1983). Transformed yeast cells were incubated in YPD broth (Sherman et al., Methods in Yeast Genetics, Cold Spring Harbor, N.Y., 1983) at 30° C. overnight prior to plating out on selective medium (YPD plus 500 μg/ml G418). This allows expression of G418-resistance and increases transformation frequency. Colonies that came up as $G418^r$ were checked on minimal medium lacking leucine (YNB+glucose+histidine+uracil+tryptophan, Sherman et al., 1983) to check for the $Leu^+$ phenotype also conferred by pWYG7HBP. Positive transformants ($G418^r$ $Leu^+$) were used for expression analysis.

5. Galactose-induction of Expression of HBP

Transformants were grown to the mid-logarithmic stage ($10^7$ cells/ml) in YP broth containing 2% raffinose and 500 μg/ml G418 at 30° C. in an orbital shaker. An aliquot of 40% galactose was then added to a final concentration of 2%, and the culture was incubated for a further 48 h. The cells were then harvested by low speed centrifugation, washed once in distilled water, and resuspended in ice-cold break buffer (20 mM sodium phosphate pH 7.0, 0.1% Triton X-100, 4 mM phenylmethanesulphonyl fluoride, 4 mM EGTA, and 2 μg/ml each of pepstatin, antipain, leupeptin, and chymostatin; 5 ml for cells from a 250 ml culture) Acid-washed glass beads (0.45 mm) were added and the cells were broken by vigorous vortexing. The crude cell lysate was cleared by centrifugation for 15 mins at 10,000 g. The protein concentration of the cleared supernatant was determined using the BioRad protein assay (BioRad, according to manufacturer's instructions), and the material was stored at −20° C. in aliquots.

6. Analysis of Cell Lysates for Expression

The proteins in the induced yeast cell lysates were analysed by separation in SDS-polyacrylamide gels (Laemmli, Nature 227, 680–685, 1970). 50 μg of soluble protein were loaded per track, and as a negative control an extract of induced S150-2B was loaded. A new protein band was detected by staining with Coomassie blue in the pWYG7HBP-transformed cell extracts, migrating at about 24,000 kDa (not shown). It was confirmed that this polypeptide is HBP by using western blot analysis with either HBcAg or BB05 antiserum (FIG. 5, result with HBcAg serum). ELISA quantitation data indicate expression levels of 10–30% of cell protein.

7. HBP Fusion Protein Expressed in Yeast Associates to Form Core Particles

In order to test whether or not the HBP protein made in yeast was present as core particles, the induced cell extract was layered over a 15%–45% w/v sucrose density gradient (in phosphate-buffered saline) and centrifuged in a Beckman SW28 rotor (28,000 rpm, 4 h). The gradient was fractionated and the fractions analysed for the presence of HBcAg- or *B. pertussis* epitope-reacting material by spotting aliquots from each gradient fraction onto a nitrocellulose grid and processing the filter as for Western blot (dot blot shown in FIG. 6).

Peak reactivity was detected in the middle fractions of the gradient, and none was detected at the top of the gradient. This indicates that all the HBP protein made in yeast associates to form core particles which sediment in a sucrose gradient. For confirmation, an aliquot from a peak gradient fraction was sent for electron microscopy (phosphotungstic acid stain). A large number of viral core particles were clearly seen (not shown)

EXAMPLE 3

Dot-blot Antibody Hybridisation

Aqueous solutions of the three peptides prepared in Example 1 (2 mg/ml) and the HBP fusion protein prepared in Example 2 were used in dot-blot antibody hydridization experiments. Briefly, 10 μl samples of the peptide or fusion protein were applied to a nitrocellulose membrane and allowed to dry on. Filter hybridzation experiments with monoclonal antibodies were carried out by normal methods (see, for example, "Antibodies, a laboratory manual" p.178, Ed. E. Marlow and D. Lane 1988, Cold Spring Harbor Laboratory). The Mabs were:

BB05 and BB07 (Montarez et al., Infect. Immun. 47, 744, 1985) which were raised against the 68 kDa protein from B. bronchiseptica but which cross-react with P.69 from B. pertussis; and a panel of 7 Mabs raised against B. pertussis.

Figure 7:
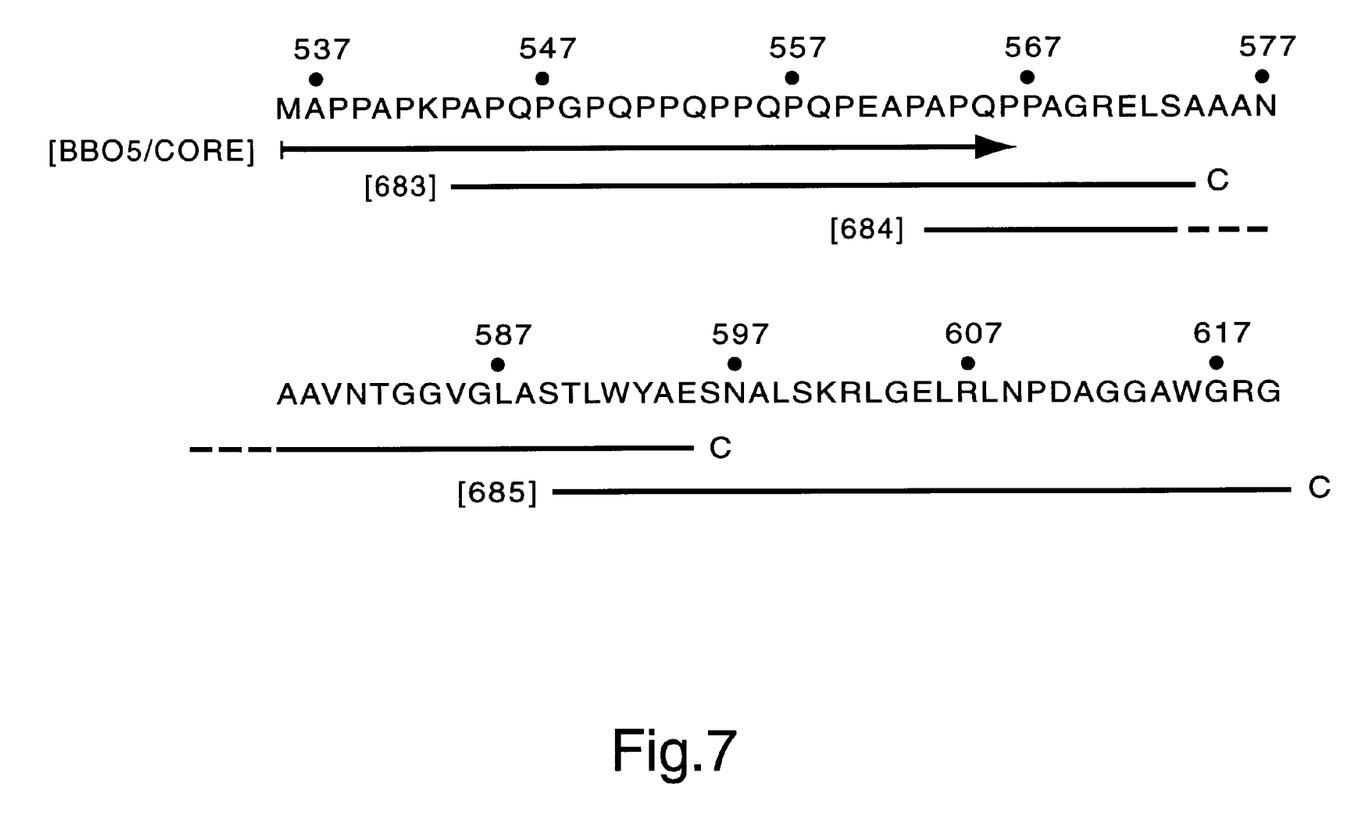
FIG. 7 shows the region of P.69 from which peptides 683, 684 and 685 and the epitope presented by the HBP fusion protein are derived. BB05/CORE binds BB05. Peptide 683 binds BB05, BB07, E4A8 and E4D7. Peptide 684: no binding. Peptide 685: binds PBE3. The numbering of the amino acid sequence refers to the residues of mature (i.e. signal sequence processed) P.69.

The results are shown in Table 1 and FIG. 7. FIG. 7 shows the region of P.69 around which the peptides were made. The three chemically synthesised peptides have an additional non-natural carboxy-terminal cysteine residue. The HBP fusion protein has a N-terminal methionine residue. The results establish that the epitope of interest lies within the region with the following sequence:

APQPGPQPPQPPQPQPEAPAPQP.

TABLE 1

|  | Monoclonal antibody | Peptide 683 | Peptide 684 | Peptide 685 | HBP fusion protein |
|---|---|---|---|---|---|
| Bordetella bronchiseptica | BB05 | + | − | − | + |
|  | BB07 | + | − | − | − |
| Bordetella pertussis | BPE3 | − | − | + | − |
|  | BPD8 | − | − | − | − |
|  | BPE8 | − | − | − | − |
|  | D5E9 | − | − | − | − |
|  | F6E5 | − | − | − | − |
|  | E4A8 | + | − | − | − |
|  | E4D7 | + | − | − | − |

EXAMPLE 4

Kendrick Test

1. Coupling of Peptides

The peptides of Example 1 were coupled to Keyhole Limpet Haemocyanin (KLH) through an added C-terminal cysteine residue using M-Maleimidobenzoyl-N-hydroxysulfosuccinimide ester (MBS) as a heterobifunctional cross-linker (Liu, F. et al, Biochemistry 18, 690, 1979). Briefly, dialysed KLH is reacted with MBS dissolved in dimethylformamide (DMF) at room temperature, then run through a G-25 column. The KLH protein peaks were pooled, and added to free peptide. The pH was then adjusted to between 7 and 7.5, and after 3 hours stirring at room temperature the coupled peptide was stored at −20° C. The KLH concentration must not exceed 20 mg/ml, MBS/KLH molar ratio is 40:1, and the final concentration of DMF in the reaction should be below 30%. Peptides 683, 684 and 685 were coupled using 2.5 mg KLH per 5 mg peptide (a ratio of 1:2 wt/wt).

2. Preparation of Filamentous Heamagglutin (FHA)

FHA can be prepared by methods well known in the art (see Arach and Munoz J. J. (1970), Infect. Immunology 25 764–767; Ashworth et al (1982) Infect. Immun. 37 1278–1281). However FHA in the following procedure was prepared in accordance with the following protocol.

FHA purification: B. pertussis Tomaha or BP357 (Tn5 transposon mutant of A. A. Weiss et al (1983) which does not secrete the LPF) were grown in Stainer & Scholte medium (0.05 Tris) in 650 ml Costar flasks (150 ml in each) for 5 days at 37° C. (Sato et al, Infection and Immunity 41, 313–320, 1983). Before centrifugation (30 mins at 6000×g) 50 μM 1,10-phenanthroline monohydrate as proteolysis inhibitor was added to the cultures. The cell free supernatant was applied to a 30×150 mm column of Hydroxylapatite (BD4) and washed (all at room temperature and a speed of pumping 500 ml/hr) sequentially with 10 mM phosphate buffer, pH 8, 100 mM phosphate buffer, pH 7.1 until stable baseline.

The retained material was eluted with 0.5 M NaCl added to the 100 mM phosphate buffer and the peak fractions agglutinating goose red blood cells were pooled. The pool was dialyzed overnight against 25–30 volumes of 0.025 M Bis.-Tris/HCl buffer at 4° C. The precipitated FHA was collected on a centrifuge (20 mins at 8000×g). The next step was inspired by Cowell et al (in vol. IV, Bacterial Vaccine, 371–379, Seminars in Infectious Disease, Weinstein and Fields: editors, Thieme Verlag, New York, Stuttgart, 1982) who found that the FHA (as well as LPF) is soluble in 40 mM beta-alanine buffer, pH 3.5. The precipitated FHA was solubilized in the smallest possible volume of 3-alanine buffer (3.57 g 3-alanine and 0.35 g formic acid per litre), insolubles removed by centrifugation and the clear supernatant was applied to a column (25×500 mm) of Ultrogel AcA 34 equilibrated and eluted with the same buffer.

The haemagglutinating material appeared in a sharp peak followed by a shoulder. The shoulder material was discarded, the fractions from the sharp peak were pooled and kept frozen or re-precipitated by dialysis against 0.025M Bis-Tris buffer and dissolved in a smaller volume of 3-alaninp buffer. The solubility is approx. 2.5 mg FHA/ml. The material frozen (at −20 or −40° C.) at acid pH appeared stable as judged from its ELISA reactivity and appearance in the SDS-PAGE gels: it formed prevalently three strong bands in the region of 150–100 KD.

3. Kendrick Test

This was performed according to W.H.O. Requirements for Pertussis Vaccine using MF1 or NIH MIce (OLAC, category 3, free of most pathogens including B. brochiseptica), weighing 14–16 g. The antigens, in 0.5 ml volumes, were inoculated concomitantly intraperitoneally and comprised a top dilution and three four-fold serial dilutions. After two weeks the mice were challenged intracerebrally using the recommended challenge strain 18–323 (100–200 $LD_{50}$). The number of survivors in each group was used for calculation of the relative potency in respect to the British Pertussis Reference Vaccine 66/84 using a program of parallel line probit analysis. The results are shown in Table 2.

TABLE 2

| Vaccine | Peptides (μg) 683 | 684 | 685 | +FHA (μg) | Survivors |
|---|---|---|---|---|---|
| 1 | 10 | 10 | 10 | 20 | 6/16 |
| 2 | 3.3 | 3.3 | 3.3 | 6.6 | 3/16 |
| 3 | 1.11 | 1.11 | 1.11 | 2.2 | 7/16 |
| 4 | 0.37 | 0.37 | 0.37 | 0.74 | 5/16 |
|  | HBP fusion Protein (μg) + FHA (μg) | | | | |
| 1 | 1 | | | 20 | 8/16 |
| 2 | 0.33 | | | 6.6 | 11/16 |
| 3 | 0.11 | | | 2.2 | 4/16 |
| 4 | 0.037 | | | 0.74 | 1/16 |
|  | FHA alone (μg) | | | | |
| 1 | | | | 20 | 3/16 |
| 2 | | | | 6.6 | 2/16 |
| 3 | | | | 2.2 | 3/16 |
| 4 | | | | 0.74 | 1/16 |

TABLE 2-continued

| | 66/88 whole cell vaccine I.U. | Survivors |
|---|---|---|
| 1 | 0.25 | 11/16 |
| 2 | 0.08 | 2/16 |
| 3 | 0.028 | 2/16 |
| 4 | 0.009 | 3/16 |

The results show clearly that the combination of FHA with either a mixture of all three chemically synthesized peptides or with the HBP fusion protein is more potent that FHA alone.

EXAMPLE 5
Epitope Mapping Using Synthetic Peptides (Pepscan)

Hexameric peptides, overlapping by one amino acid residue, were synthesised on solid phase polyethylene pins as described by Geysen et al (PNAS USA 81, 1984, 3998–4002). Ninety four hexameric peptides were synthesised, covering residues 505 to 603 of the P.69 antigen of B. pertussis. Pepscan peptide 1 was Thr(505)-Asp(510). Pepscan peptide 94 was Ala(598)-Leu(603).

Reactivity of the peptides to monoclonal antibody (mAb) BB05 was determined by incubation of the pins in antibody for 1–2 hrs or overnight, followed by washing and incubation in peroxidase conjugated goat-antimouse antibody. The mAb BB05 is an (IgG1) raised against the P.68 antigen from B. bronchiseptica (Montarez et al, Infect. Immun. 47, 1985, 644–751). This mAb is a neutralising mAb which cross-reacts with P.69 from B. pertussis.

Enzyme reactivity was determined by incubation of the pins in ABTS substrate solution (50 mg azino-di-3-ethyl-benzthiazodinsulphonate (ABTS) in 100 ml buffer (0.1 molar disodium hydrogen orthophosphate, 0.08 molar citric acid, pH 4.0 containing 30 μl hydrogen peroxide)), and the $A_{420}$ of the solution measured after 10–60 minutes using a Titertek Multiscan MC1100. Pins were sonicated for 30 min at 65° C. in 0.1M $Na_2HPO_4$, 0.1% SDS, 0.01 M B-mercaptoethanol to remove bound antibody and stain complexes prior to incubation in subsequent antibody. The results are shown in FIG. 8.

Figure 8:
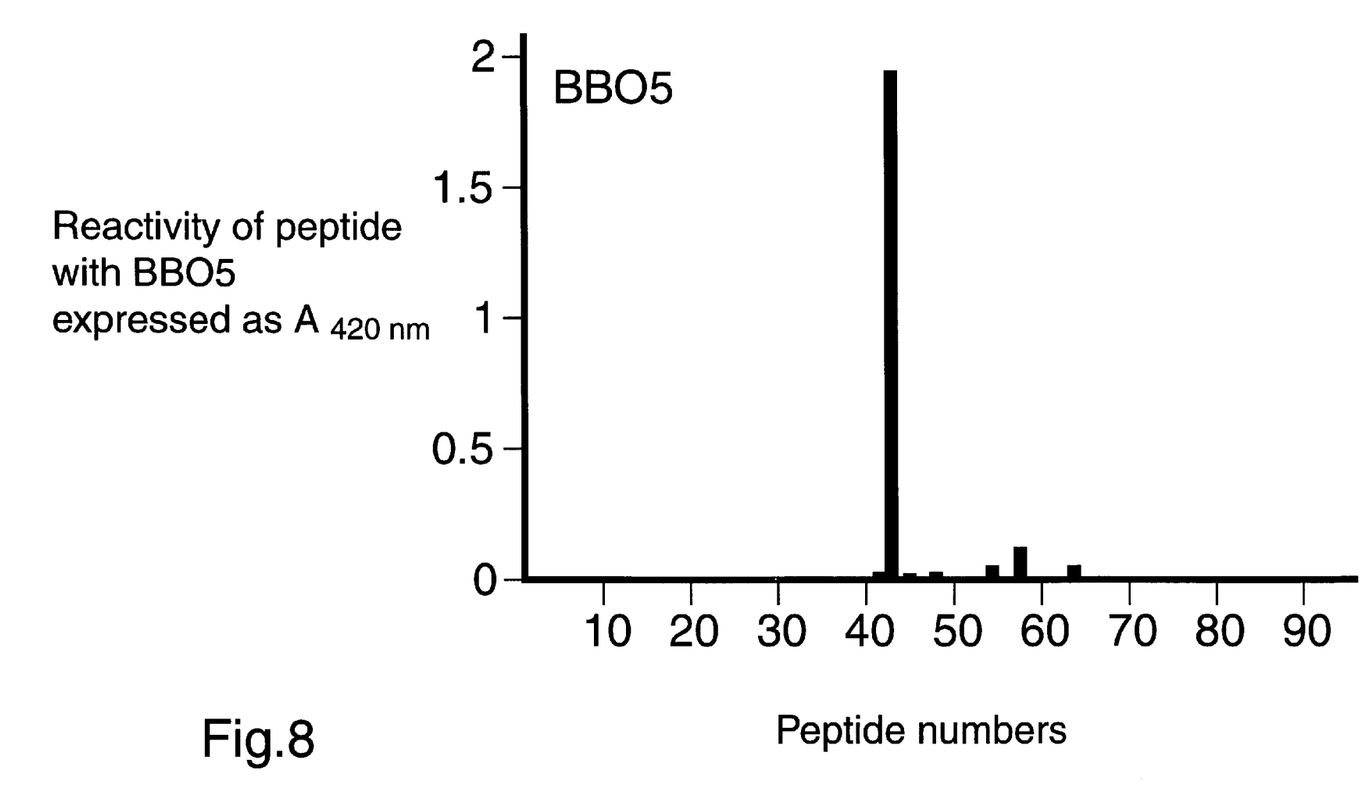
FIG. 8 shows the analysis of peptides, covering residues 505 to 603 of the P.69 protein of B. pertussis, with monoclonal antibody.

As can be seen from FIG. 8, mAb BB05 recognised only Pepscan peptide 43 (sequence PGPQPP). This is consistent with recognition of peptide 683 and located the BB05 epitope in the region of the (Pro-Gln-Pro)$_5$ repeats of P.69.

We claim:
1. A polypeptide which is up to 50 amino acid residues long and which is a fragment of the P69 antigen of Bordetella pertussis, said polypeptide comprising the amino acid sequence Pro-Gly-Pro-Gln-Pro-Pro.

2. A polypeptide according to claim 1 which comprises the sequence Ala-Pro-Gln-Pro-Gly-Pro-Gln-Pro-Pro-Gln-Pro-Pro-Gln-Pro-Gln-Pro-Glu-Ala-Pro-Ala-Pro-Gln-Pro.

3. A conjugate comprising
    a polypeptide which is up to 50 amino acid residues long and which is a fragment of the P69 antigen of Bordetella pertussis, said polypeptide comprising the amino acid sequence Pro-Gly-Pro-Gln-Pro-Pro, and
    a physiologically acceptable carrier linked to said polypeptide.

4. A conjugate according to claim 3 wherein the polypeptide comprises the sequence Ala-Pro-Gln-Pro-Gly-Pro-Gln-Pro-Pro-Gln-Pro-Pro-Gln-Pro-Gln-Pro-Glu-Ala-Pro-Ala-Pro-Gln-Pro.

5. A fusion protein comprising a carrier protein and, fused thereto, a polypeptide which is up to 50 amino acid residues long and which is a fragment of the P69 antigen of Bordetella pertussis, said polypeptide comprising the amino acid sequence Pro-Gly-Pro-Gln-Pro-Pro.

6. A fusion protein according to claim 5 wherein the polypeptide comprises the sequence Ala-Pro-Gln-Pro-Gly-Pro-Gln-Pro-Pro-Gln-Pro-Pro-Gln-Pro-Gln-Pro-Glu-Ala-Pro-Ala-Pro-Gln-Pro.

7. A polypeptide which is up to 50 amino acids long, which comprises the amino acid sequence Pro-Gly-Pro-Gln-Pro-Pro, and which is a fragment of an antigen selected from the group consisting of the P68 antigen of Bordetella bronchiseptica and the P70 antigen of Bordetella parapertussis.

8. A polypeptide according to claim 7, which comprises a sequence selected from the group consisting of Ala Pro Gln Pro Gly Pro Gln Pro Gly Pro Gln Pro Pro Gln Pro Pro Gln Pro Pro Gln Pro Pro Gln Pro Pro Gln Pro Pro Gln Arg Gln Pro Glu Ala Pro Ala Pro Gln Pro; and Ala Pro Gln Pro Gly Pro Gln Pro Gly Pro Gln Pro Pro Gln Pro Pro Gln Pro Pro Gln Pro Pro Gln Pro Pro Gln Arg Gln Pro Glu Ala Pro Ala Pro Gln Pro.

9. A conjugate comprising
    a polypeptide which is up to 50 amino acids long, which comprises the amino acid sequence Pro-Gly-Pro-Gln-Pro-Pro, and which is a fragment of an antigen selected from the group consisting of the P68 antigen of Bordetella bronchiseptica and the P70 antigen of Bordetella parapertussis; and
    a physiologically acceptable carrier linked to said polypeptide.

10. A conjugate according to claim 9 wherein the polypeptide comprises a sequence selected from the group consisting of
    Ala Pro Gln Pro Gly Pro Gln Pro Gly Pro Gln Pro Pro Gln Pro Pro Gln Pro Pro Gln Pro Pro Gln Pro Pro Gln Pro Pro Gln Arg Gln Pro Glu Ala Pro Ala Pro Gln Pro; and Ala Pro Gln Pro Gly Pro Gln Pro Gly Pro Gln Pro Pro Gln Pro Pro Gln Pro Pro Gln Pro Pro Gln Arg Gln Pro Glu Ala Pro Ala Pro Gln Pro.

11. A fusion protein comprising a carrier protein and, fused thereto, a polypeptide which is up to 50 amino acid residues long, which comprises the amino acid sequence Pro-Gly-Pro-Gln-Pro-Pro, and which is a fragment of an antigen selected from the group consisting of the P68 antigen of Bordetella bronchiseptica and the P70 antigen of Bordetella parapertussis.

12. A fusion protein according to claim 11 wherein the polypeptide comprises a sequence selected from the group consisting of
    Ala Pro Gln Pro Gly Pro Gln Pro Gly Pro Gln Pro Pro Gln Pro Pro Gln Pro Pro Gln Pro Pro Gln Pro Pro Gln Arg Gln Pro Glu Ala Pro Ala Pro Gln Pro; and Ala Pro Gln Pro Gly Pro Gln Pro Gly Pro Gln Pro Pro Gln Pro Pro Gln Pro Pro Gln Arg Gln Pro Glu Ala Pro Ala Pro Gln Pro.

13. A fusion protein according to claim 5 or 11 wherein the carrier is hepatitis B core antigen and the polypeptide is fused to the amino terminus of the antigen.

14. A fusion protein according to claim 13, wherein the sequence of the polypeptide is Met Ala Pro Pro Ala Pro Lys Pro Ala Pro Gln Pro Gly Pro Gln Pro Pro Gln Pro Pro Gln Pro Gln Pro Glu Ala Pro Ala Pro Gln Pro.

15. A vaccine comprising a pharmaceutically acceptable carrier or diluent, a polypeptide as defined in claim 1 or 7 and filamentous haemagglutinin.

16. A vaccine comprising a pharmaceutically acceptable carrier or diluent, a conjugate as defined in claim 3 or 9 and filamentous haemagglutinin.

17. A vaccine comprising a pharmaceutically acceptable carrier or diluent, a fusion protein as defined in claim 5 or 11 and filamentous haemagglutinin.

18. A method of vaccinating a host against *Bordetella pertussis*, which method comprises administering to said host an effective amount of filamentous haemagglutinin and a polypeptide as defined in claim 1.

19. A method of vaccinating a host against *Bordetella pertussis*, which method comprises administering to said host an effective amount of filamentous haemagglutinin and a conjugate as defined in claim 3.

20. A method of vaccinating a host against *Bordetella pertussis*, which method comprises administering to said host an effective amount of filamentous haemagglutinin and a fusion protein as defined in claim 5.

* * * * *

UNITED STATES PATENT AND TRADEMARK OFFICE
CERTIFICATE OF CORRECTION

PATENT NO. : 5,976,544

DATED : November 2, 1999

INVENTOR(S) : Ian George Charles, et al.

It is certified that error appears in the above-identified patent and that said Letters Patent is hereby corrected as shown below:

On the title page, Item [75] add as an inventor: --Michael A. Romanos--.

Signed and Sealed this

Eighth Day of August, 2000

Attest:

Q. TODD DICKINSON

*Attesting Officer*     *Director of Patents and Trademarks*